US008765776B2

(12) United States Patent
Kim et al.

(10) Patent No.: US 8,765,776 B2
(45) Date of Patent: Jul. 1, 2014

(54) ANTIHYPERTENSIVE PHARMACEUTICAL COMPOSITION

(75) Inventors: Seung Ho Kim, Seoul (KR); Ji Han Kim, Seoul (KR); Je Hak Kim, Anyang-si (KR); Kyung Wan Nam, Gunpo-si (KR); Yong Ha Chi, Yongin-si (KR); Joo Han Lee, Seoul (KR); Soo Heui Paik, Ansan-si (KR); So Jeong Yi, Seoul (KR); Tae Eun Kim, Seoul (KR); Seo Hyun Yoon, Seoul (KR); Joo Youn Cho, Seoul (KR); Sang Goo Shin, Seoul (KR); In Jin Jang, Seoul (KR); Kyung Sang Yu, Seoul (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 211 days.

(21) Appl. No.: 13/205,545

(22) Filed: Aug. 8, 2011

(65) Prior Publication Data
US 2012/0264772 A1 Oct. 18, 2012

(30) Foreign Application Priority Data

Apr. 12, 2011 (KR) .................. 10-2011-0033856

(51) Int. Cl.
*A01N 43/54* (2006.01)
*A61K 31/505* (2006.01)
*A01N 43/40* (2006.01)
*A61K 31/44* (2006.01)
*C07D 239/02* (2006.01)
*C07D 211/72* (2006.01)
*C07D 211/84* (2006.01)
*C07D 213/62* (2006.01)
*C07D 213/78* (2006.01)

(52) U.S. Cl.
USPC ............ 514/269; 514/349; 544/319; 546/299

(58) Field of Classification Search
USPC ................. 514/269, 349; 544/319; 546/299
See application file for complete search history.

(56) References Cited

U.S. PATENT DOCUMENTS

| 4,572,909 | A | 2/1986 | Campbell et al. | 514/356 |
| 5,869,476 | A | 2/1999 | Paik et al. | 514/183 |
| 6,294,542 | B1 | 9/2001 | Lee et al. | 514/269 |
| 7,309,788 | B2 | 12/2007 | Kim et al. | 544/319 |

FOREIGN PATENT DOCUMENTS

| EP | 0 253 310 | 1/1988 |
| KR | 1989-0011854 | 8/1989 |
| KR | 2001-0079517 | 8/2001 |
| KR | 2001-0090193 | 10/2001 |
| KR | 10-0354654 | 9/2002 |
| KR | 2004-0032639 | 4/2004 |
| KR | 10-0521980 | 10/2005 |
| KR | 2010-0048137 | 5/2010 |
| KR | 2011-0086293 | 7/2011 |
| WO | WO 99/55681 | 11/1999 |
| WO | WO 00/02543 | 1/2000 |
| WO | WO 00/16773 | 3/2000 |
| WO | WO 03024956 A1 * | 3/2003 |
| WO | WO 2007001066 A1 * | 1/2007 |
| WO | WO 2012/141385 | 10/2012 |

OTHER PUBLICATIONS

Letter/Written Disclosure of the Supplemental Information Disclosure Statement for the above-referenced application, mailed on Jan. 19, 2012, 2 pages.
Adis R&D Insight database, "Fimasartan," [No authors listed] Am J Cardiovasc Drugs 11(4):249-252 (2011).
Boryung Pharmaceutical Co., Ltd., "Fimasartan: new generation of ARBs," Published on Jun. 2010 [online][retrieved on Nov. 22, 2011] Retrieved from:<URL:kobio.org [11 pages].
Chi et al., "Safety, tolerability, pharmacokinetics, and pharmacodynamics of fimasartan following single and repeated oral administration in the fasted and fed states in healthy subjects." Am J Cardiovasc Drugs 11(5):335-346 (2011).
ClinicalTrials.gov, "A clinical study to evaluate efficacy and safety of fimasartan/hydrochlorothiazide combination-therapy," Boryung Pharmaceutical Co., Ltd. Published on Oct. 10, 2010 [online][retrieved on Nov. 22, 2011] Retrieved from:<URL:clinicaltrials.gov/ct2/show/NCT01258673 [1 page].
ClinicalTrials.gov, "A therapeutic exploratory clinical study to evaluate the antihypertensive efficacy of fimasartan (BR-A-657•K) during 24 hours in patients with mild to moderate essential hypertension," Boryung Pharmaceutical Co., Ltd. Published on Jun. 16, 2009 [online][retrieved on Nov. 22, 2011] Retrieved from:<URL:clinicaltrials.gov/ct2/show/NCT0092241 [1 page].
ClinicalTrials.gov, "Efficacy, safety and pharmacodynamic/pharmacokinetic study of fimasartan (BR-A-657•K)",Boryung Pharmaceutical Co., Ltd. Published on Jul. 10, 2009 [online][retrieved on Nov. 22, 2011] Retrieved from:<URL:clinicaltrials.gov/ct2/show/NCT00937651 [4 pages].
ClinicalTrials.gov, "Fimasartan (BR-A-657) multiple oral dose in healthy subjects," Boryung Pharmaceutical Co., Ltd. Published on Dec. 14, 2010 [online][retrieved on Nov. 22, 2011] Retrieved from:<URL:clinicaltrialsfeeds.org/clinical-trials/show/NCT01289899 [1 page].
ClinicalTrials.gov, "Study to compare and assess the safety and pharmacokinetic characteristics after oral administration of fimasartan (BR-A-657•K) in healthy elderly and young male volunteers," Boryung Pharmaceutical Co., Ltd. Published on Jul. 6, 2009 [online][retrieved on Nov. 22, 2011] Retrieved from:<URL:txooo.im/ct2/show/NCT00937534 [3 pages].

(Continued)

*Primary Examiner* — Sarah Pihonak
(74) *Attorney, Agent, or Firm* — McKenna Long & Aldridge LLP; Stephanie Seidman; Frank Miskiel

(57) ABSTRACT

Provided is an antihypertensive pharmaceutical composition containing Fimasartan, a pharmaceutically acceptable salt thereof, a solvate thereof or a hydrate thereof as an angiotensin II receptor blocker, and Amlodipine, an isomer thereof, a pharmaceutically acceptable salt thereof, a solvate thereof or a hydrate thereof as a calcium channel blocker.

20 Claims, No Drawings

(56) References Cited

OTHER PUBLICATIONS

ClinicalTrials.gov, "A study to evaluate the pharmacokinetic drug interaction after oral concurrent administration of fimasartan and amlodipine in healthy male volunteers," Boryung Pharmaceutical Co., Ltd. Published on Jul. 10, 2009 [online][retrieved on Nov. 22, 2011] Retrieved from:<URL:clinicaltrials.gov/ct2/show/ NCT01258673 [3 pages].
Collins et al., "Blood pressure, stroke, and coronary heart disease. Part 2, Short-term reductions in blood pressure: overview of randomised drug trials in their epidemiological context," Lancet 335(8693):827-838 (1990).
Derwent English abstract for WO 2000/016773 (equivalent document for KR 10-0354654), published Sep. 8, 1999 entitled: "Composition for reducing treating hypertension or platelet aggregation disorders, contains angiotensin II receptor antagonist and platelet anti-aggregation agent," Dialog File No. 351, Accession No. 9957323 [3 pages].
English language abstract of Korean Patent Publication No. KR 2001-0090193 (Item AG), Korean Intellectual Property Office, 2 pages.
English language abstract of Korean Patent Publication No. KR 2004-0032639 (Item AH), issued as Korean Patent No. KR 0521980 (Item AL), Korean Intellectual Property Office, 2 pages.
English language abstract of Korean Patent Publication No. KR 2010-0048137 (Item AI), Korean Intellectual Property Office, 1 page.
English language abstract of Korean Patent Publication No. KR 2011-0086293 (Item AJ), Korean Intellectual Property Office, 1 page.
MacGregor et al., "Captopril in essential hypertension; contrasting effects of adding hydrochlorothiazide or propranolol," Br Med J. (Clin Res Ed) 284(6317):693-696 (1982).
Shin et al., "Simultaneous determination of fimasartan, a novel antihypertensive agent, and its active metabolite in rat plasma by liquid chromatography-tandem mass spectrometry," Biomed Chromatogr. Jan. 26, 2011[Epub ahead of print]—Abstract only 1 page.
Shin et al., "The effect of the newly developed angiotensin receptor II antagonist fimasartan on the pharmacokinetics of atorvastatin in relation to OATP1B1 in healthy male volunteers," J Cardiovasc Pharmacol. Jul. 14, 2011[Epub ahead of print] Abstract only 1 page.
Waeber, B. and H. Brunner, "Combination antihypertensive therapy: does it have a role in rational therapy?" Am J Hypertens. 10(7 Pt 2):131S-137S (1997).
Yi et al., "Effect of multiple doses of fimasartan, an angiotensin II receptor antagonist, on the steadystate pharmacokinetics of digoxin in healthy volunteers." Int J Clin Pharmacol Ther. 49(5):321-327 (2011).
Letter/Written Disclosure of the Information Disclosure Statement for the above-referenced application, mailed on Jun. 5, 2013, 2 pages.
"Kanarb (Fimasartan)" brochure, Boryung Pharmaceutical Co., Ltd., Retrieved from:<URL:test.kanarb.com/include/download. asp?strUpFile=english.jpg [retrieved on May 31, 2013], 1 page.
Chrysant et al., "The combination of olmesartan medoxomil and amlodipine besylate in controlling high blood pressure: COACH, a randomized, double-blind, placebo-controlled, 8-week factorial efficacy and safety study," Clinical Therapeutics 30(4):587-604 (2008).
Clinical Trial: "A multicenter, phase 3 study to evaluate the antihypertensive efficacy and safety of Fimasartan(BR-A-657•K) 30mg compared to placebo in patients with mild to moderate essential hypertension (fimasartan)," Boryung Pharmaceutical Co., Ltd. Retrieved from:<URL:clinicaltrials.gov/ct2/show/NCT01672476 [accessed May 31, 2013; First Received Aug. 26, 2012; last updated Sep. 4, 2012] 5 pages.
Clinical Trial: "A randomized, double-blind, placebo-controlled, 3×3 factorial design, phase II study to evaluate the antihypertensive efficacy and safety of combination of funasartan and amlodipine in patients with essential hypertension," Boryung Pharmaceutical Co., Ltd. Retrieved from:<URL:clinicaltrials.gov/ct2/show/ NCT01518998?term=NCT01518998 [accessed May 31, 2013; First Received Jan. 24, 2012; last updated Mar. 26, 2013] 5 pages.
Clinical Trial: "Clinical trials for single oral dose of 60mg fimasartan and single IV infusion of 30mg Fimasartan to evaluate the absolute bioavailability of Kanarb® tablet (Fimasartan) in healthy subjects," Boryung Pharmaceutical Co., Ltd. Retrieved from:<URL:clinicaltrials.gov/ct2/show/NCT01671020 [accessed May 31, 2013; First Received Aug. 20, 2012; last updated Aug. 22, 2012] 2 pages.
Ferri et al., "Role of combination therapy in the treatment of hypertension: focus on valsartan plus amlodipine." Advances in Therapy. 25(4):299-319 (2008).
Gu et al., "The effect of fimasartan, an angiotensin receptor type 1 blocker, on the pharmacokinetics and pharmacodynamics of warfarin in healthy Korean male volunteers: a one-sequence, two-period crossover clinical trial." Clin Ther. 34(7):1592-1600 (2012).
Jeon et al., "Assessment of the drug-drug interactions between ftmasartan and hydrochlorothiazide in healthy volunteers." J Cardiovasc Pharmacol. 59(1):84-91 (2012).
Kanarb website, Clinical Trials—Overview, Boryung Pharmaceutical Co., Ltd., Retrieved from:<URL:test.kanarb.com/clinical_trials/ overview.asp [retrieved on May 31, 2013] 1 page.
Kanarb website, Clinical Trials—Results, Boryung Pharmaceutical Co., Ltd., Retrieved from:<URL:test.kanarb.com/clinical_trials/results.asp [retrieved on May 31, 2013] 1 page.
Kanarb website, Fimasartan—History, Boryung Pharmaceutical Co., Ltd., Retrieved from:<URL:test.kanarb.com/fimasartan/history.asp [retrieved on May 31, 2013] 1 page.
Kanarb website, Fimasartan—Kanarb, Boryung Pharmaceutical Co., Ltd., Retrieved from:<URL:test.kanarb.com/fimasartan/kanarb.asp [retrieved on May 31, 2013] 1 page.
Kanarb website, Fimasartan—Overview, Boryung Pharmaceutical Co., Ltd., Retrieved from:<URL:test.kanarb.com/fimasartan/overview.asp [retrieved on May 31, 2013] 1 page.
Kanarb website, Nonclinical trials—Overview, Boryung Pharmaceutical Co., Ltd., Retrieved from:<URL:test.kanarb.coin/non_ clinical_trials/overview.asp [retrieved on May 31, 2013] 1 page.
Kanarb website, Nonclinical trials—Pharmacokinetics, Boryung Pharmaceutical Co., Ltd., Retrieved from:<URL:.kanarb.com/non_ clinical_trials/Pharmacokinetics.asp [retrieved on May 31, 2013] 1 page.
Kanarb website, Nonclinical trials—Pharmacology, Boryung Pharmaceutical Co., Ltd., Retrieved from:<URL:test.kanarb.com/non_ clinical_trials/pharmacology.asp [retrieved on May 31, 2013] 2 pages.
Kanarb website, Nonclinical trials—Toxicology, Boryung Pharmaceutical Co., Ltd., Retrieved from:<URL:test.kanarb.com/non_ clinical_trials/toxicology.asp [retrieved on May 31, 2013] 1 page.
Kim et al., "Fimasartan, a novel angiotensin II receptor antagonist." Arch Pharm Res.35(7):1123-1126 (2012).
Kim et al., "Increased Systemic Exposure of Fimasartan, an Angiotensin II Receptor Antagonist, by Ketoconazole and Rifampicin." The Journal of Clinical Pharmacology 53(1):75-81 (2013).
Kim et al., "Synthesis and antihypertensive activity of pyrimidin-4(3H)-one derivatives as losartan analogue for new angiotensin II receptor type 1 (ATI) antagonists." Bioorg Med Chem Lett. 22(4):1649-1654(2012).
Lee et al., "Effect of age on the pharmacokinetics of fimasartan (BR-A-657)," Expert Opin Drug Metab Toxicol. 7(11):1337-1344 (2011) (Abstract Only).
Ryu et al., "Fimasartan, anti-hypertension drug, suppressed inducible nitric oxide synthase expressions via nuclear factor-kappa B and activator protein-1 inactivation." Biol Pharm Bull. 36(3):467-474 (2013).
Shin et al., "Simultaneous determination of fimasartan, a novel antihypertensive agent, and its active metabolite in rat plasma by liquid chromatography-tandem mass spectrometry." Biomed Chromatogr. 25(11):1208-1214 (2011).
Shin et al., "The effect of the newly developed angiotensin receptor II antagonist fimasartan on the pharmacokinetics of atorvastatin in relation to OATP1B1 in healthy male volunteers," J Cardiovasc Pharmacol. 58(5):492-499 (2011).

(56) References Cited

OTHER PUBLICATIONS

Stangier et al., "Pharmacokinetics of repeated oral doses of amlodipine and amlodipine plus telmisartan in healthy volunteers," The Journal of Clinical Pharmacology 40(12):1347-1354 (2000).
Yi et al., "Pharmacokinetic interaction of fimasartan, a new angiotensin II receptor antagonist, with amlodipine in healthy volunteers," J Cardiovasc Pharmacol 57(6):682-689 (2011).
International Search Report, issued Apr. 4, 2012, in connection with corresponding International Application No. PCT/KR2011/005754, 4 pages.
Letter/Written Disclosure of the Information Disclosure Statement for the above-referenced application, mailed on Dec. 4, 2013, 2 pages.
Boryung Pharmaceutical Co., Ltd., "R&D: Pipeline, Fimasartan," Published on Oct. 11, 2005 [online][retrieved on Nov. 11, 2013] Retrieved from:<URL:boryung.co.kr/englishV2/rnd/rnd43.asp, 1 page.
Chi et al., "Pharmacological characterization of BR-A-657, a highly potent nonpeptide angiotensin II receptor antagonist." Biol Pharm Bull. 36(7):1208-1215 (2013).
Clinical Trial: "A clinical trial to compare and evaluate the pharmacokinetic characteristics and the safety of Fimasartan in hepatic impairment patients and healthy volunteers," first received Jun. 17, 2010; last updated Jan. 2, 2012[online][retrieved on Nov. 12, 2013] Retrieved from:<URL:clinicaltrials.gov/ct2/show/NCT01146938?term=fimasartan&rank=10, 3 pages.
Clinical Trial: "A clinical trial to compare and evaluate the pharmacokinetic characteristics and the safety of Fimasartan in renal patients and healthy volunteers," first received Jun. 21, 2010; last updated Jan. 6, 2012[online][retrieved on Nov. 12, 2013] Retrieved from:<URL:clinicaltrials.gov/ct2/show/NCT01148368?term=fimasartan&rank=13 , 3 pages.
Clinical Trial: "A clinical trial to evaluate the effect of Fimarsartan on pharmacodynamics, pharmacokinetics, and the safety of warfarin in healthy male volunteers," first received Jul. 10, 2009; last updated Oct. 7, 2009[online][retrieved on Nov. 12, 2013] Retrieved from:<URL:clinicaltrials.gov/ct2/show/NCT00938132?term=fimasartan&rank=27, 2 pages.
Clinical Trial: "A randomized trial of angiotensin Receptor bLocker,Fimasartan, in aortic stenosis (ALFA Trial)," Boryung Pharmaceutical Co., first received Apr. 29, 2012; last updated Apr. 30, 2012[online][retrieved on Nov. 12, 2013] Retrieved from:<URL:clinicaltrials.gov/ct2/show/NCT01589380?term=fimasartan&rank=7 , 6 pages.
Clinical Trial: "A study to assess food effect on the pharmacokinetics of Fimasartan in healthy male volunteers," Boryung Pharmaceutical Co., Ltd., first received Nov. 2, 2009; last updated Dec. 23, 2009[online][retrieved on Nov. 12, 2013] Retrieved from:<URL:clinicaltrials.gov/ct2/show/NCT01007409?term=fimasartan&rank=15, 2 pages.
Clinical Trial: "A study to evaluate the effect of atorvastatin on the pharmacokinetics of Fimasartan in healthy male volunteers," Boryung Pharmaceutical Co., Ltd. first received Oct. 7, 2009; [online][retrieved on Nov. 12, 2013] Retrieved from:<URL:clinicaltrials.gov/ct2/show/NCT00991705?term=fimasartan&rank=21, 3 pages.
Clinical Trial: "A study to evaluate the effect of Fimasartan on pharmacokinetics, and the safety of digoxin in healthy male volunteers," Boryung Pharmaceutical Co., Ltd., first received Oct. 7, 2009; last updated Nov. 2, 2009[online][retrieved on Nov. 12, 2013] Retrieved from:<URL:clinicaltrials.gov/ct2/show/NCT00991783?term=fimasartan&rank=23, 2 pages.
Cinical Trial: "A study to evaluate the effect of Ketoconazole and Rifampicin on the pharmacokinetics of Fimasartan in healthy male volunteers," Boryung Pharmaceutical Co., Ltd., first received Jul. 10, 2009; last updated Oct. 7, 2009[online][retrieved on Nov. 12, 2013] Retrieved from:<URL:clinicaltrials.gov/ct2/show/NCT00938262?term=fimasartan&rank=26, 2 pages.
Clinical Trial: "A trial of Fimasartan for early diatolic heart failure (FINE)," Boryung Pharmaceutical Co., Ltd., first received Sep. 20, 2012; last updated Nov. 19, 2012 [online][retrieved on Nov. 12, 2013] Retrieved from:<URL:clinicaltrials.gov/ct2/show/NCT01691118?term=fimasartan&rank=25, 4 pages.
Clinical Trial: "A valsartan 80 mg-referenced, therapeutic exploratory clinical study to evaluate the antihypertensive efficacy of Fimasartan 30 mg during 24 hours in patients with mild to moderate essential hypertension," Boryung Pharmaceutical Co., Ltd., first received May 31, 2013; last updated Jun. 13, 2013[online][retrieved on Nov. 12, 2013] Retrieved from:<URL:clinicaltrials.gov/ct2/show/NCT01878201?term=fimasartan&rank=12, 4 pages.
Cinical Trial: "Antihypertensive efficacy and tolerability and determine the adequate antihypertensive dosage of Fimasartan in mild to moderate essential hypertesnsion patients," Boryung Pharmaceutical Co., Ltd., first received Jun. 16, 2009; last updated Jun. 17, 2009[online][retrieved on Nov. 12, 2013] Retrieved from:<URL:clinicaltrials.gov/ct2/show/NCT00923611?term=fimasartan&rank=9, 4 pages.
Cinical Trial: "Clinical study to evaluate the antihypertensive efficacy and changes of neurohormonal markers of Fimasartan and Atenolol with exaggerated blood pressure response during exercise in essential hypertensive patients," Boryung Pharmaceutical Co., Ltd., first received Nov. 19, 2012; last updated May 28, 2013[online][retrieved on Nov. 12, 2013] Retrieved from:<URL:clinicaltrials.gov/ct2/show/NCT01736488?term=fimasartan&rank=, 4 pages.
Cinical Trial: "Clinical Study to evalute the antihypertensive efficacy and safety of Fimasartan in Hypertension patients," Boryung Pharmaceutical Co., Ltd., first received Jun. 16, 2009; last updated Oct. 17, 2009[online][retrieved on Nov. 12, 2013] Retrieved from:<URL:clinicaltrials.gov/ct2/show/NCT00922480?term=fimasartan&rank=24, 4 pages.
Cinical Trial: "Effect of Fimasartan for modification of Atheroma vulnerability in DEFERred Coronary Disease (FIMA-DEFER)," Boryung Pharmaceutical Co., Ltd., first received Jun. 24, 2011; last updated JAug. 7, 2012[online][retrieved on Nov. 12, 2013] Retrieved from:<URL:clinicaltrials.gov/ct2/show/NCT01384747?term=fimasartan&rank=20, 4 pages.
Cinical Trial: "Fimasartan (BR-A-657) single oral dose in healthy subjects," Boryung Pharmaceutical Co., Ltd., first received Dec. 13, 2010; last updated Feb. 3, 2011[online][retrieved on Nov. 12, 2013] Retrieved from:<URL:clinicaltrials.gov/ct2/show/NCT01289886?term=fimasartan&rank=19, 3 pages.
Cinical Trial: "Study to compare and assess the safety and pharmacokinetic characteristics after oral administration of Fimasartan (BR-A-657•K) in healthy elderly and young male volunteers," Boryung Pharmaceutical Co., Ltd., first received Jul. 6, 2009; last updated Nov. 2, 2009[online][retrieved on Nov. 12, 2013] Retrieved from:<URL:clinicaltrials.gov/ct2/show/NCT00937534?term=fimasartan&rank=3, 3 pages.
Cinical Trial: "The clinical study to evaluate the efficacy and safety of Fimasartan in patients with mild to moderate essential hypertension," Boryung Pharmaceutical Co., Ltd., first received May 31, 2010; last updated Aug. 22, 2012[online][retrieved on Nov. 12, 2013] Retrieved from:<URL:clinicaltrials.gov/ct2/show/NCT01135212?term=fimasartan&rank=8, 4 pages.
Cinical Trial: "To evaluate the pharmacokinetic interactions and safety between Fimasartan and Rosuvastatin," Boryung Pharmaceutical Co., Ltd., first received Aug. 8, 2013; last updated Oct. 20, 2013[online][retrieved on Nov. 12, 2013] Retrieved from:<URL:clinicaltrials.gov/ct2/show/NCT01921946?term=fimasartan&rank=17, 3 pages.
Heart and Stroke Foundation Press Release, "Guideline alert for blood pressure patients as treatment combo fails," Published Jan. 16, 2009 [online][retrieved on Nov. 22, 2013] Retrieved from:<URL:heartandstroke.com/site/apps/nInet/content2.aspx?c=ikIQLcMWJtE&b=3485819&ct=6501933, 1 page.
Ontarget Investigators et al., "Telmisartan, ramipril, or both in patients at high risk for vascular events," N Engl J Med. 358(15):1547-1559 (2008).
International Preliminary Report on Patentability, issued Oct. 15, 2013, in connection with corresponding International Application No. PCT/ICR2011/005754, 6 pages.

* cited by examiner

ANTIHYPERTENSIVE PHARMACEUTICAL COMPOSITION

RELATED APPLICATIONS

Benefit of priority is claimed to Korean Patent Application No. 10-2011-0033856, to Seung Ho KIM, Ji Han KIM, Je Hak KIM, Kyung Wan NAM, Yong Ha CHI, Joo Han LEE and Soo Heui PAIK, entitled "ANTIHYPERTENSIVE PHARMACEUTICAL COMPOSITION," filed Apr. 12, 2011, the subject matter of which is incorporated by reference in its entirety.

TECHNICAL FIELD

The present invention relates to an antihypertensive pharmaceutical composition.

BACKGROUND ART

Hypertension is one of the most common cardiovascular diseases. Typically, a person is diagnosed with hypertension when his/her blood pressure is in a range of 140/90 mmHg. Recently, the incidence of lifestyle-related diseases such as hypertension has rapidly increased. As hypertension may result in the occurrence of acute heart diseases or myocardial infarction, there is a continued need for development of a more effective antihypertensive agent.

According to various clinical trials of antihypertensive agents, it was found that lowering of blood pressure of hypertensive patients leads to a decrease in mortality and morbidity of heart diseases or myocardial infarction (Collins R, Peto R, MacMahon S, Hebert P, Fiebach N H, Eberlein K A, Godwin J, Qizilbash N, Taylor J O, Hennekens C H, Lancet 1990, 335(8693):827-38). Although a variety of drugs have been used and administered for the purpose of treating such a clinical condition, suitable control of blood pressure is not always successful (Waeber B, Brunner H R, Am. J. Hypertens 1997. 10(7 Pt 2):131S-137S).

Among various applicable administration modes of antihypertensive drugs, a combination preparation or combination therapy of drugs is one method for achieving desired therapeutic results. On the other hand, arbitrary selection of various classes of antihypertensive agents for application of drugs to combination therapy prescription does not always provide help to achieve a desired blood pressure level in a hypertensive mammal including a human (MacGregor G A, Markandu N D, Banks R A, Bayliss J. Roulston J E, Jones J C, Br Med J (Clin Res Ed), 284 (6317): 693-6).

To this end, there is an obvious need for further development of therapeutic methods, combination preparations and pharmaceutical compositions against hypertension.

Fimasartan, which is chemically defined as 2-n-butyl-5-dimethylaminothiocarbonyl-methyl-6-methyl-3-[[2'-(1H-tetrazol-5-yl)biphenyl-4-yl]methyl]pyrimidin-4(3H)-one and has the following structural formula:

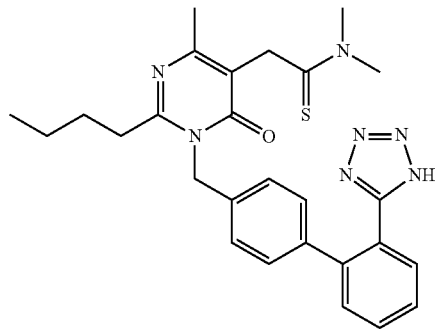

[Fimasartan]

is an antihypertensive agent of the angiotensin II receptor blocker (ARB) class and has currently been approved as a pharmaceutical product under brand name of KANARB®.

According to the randomized double-blind clinical testing conducted for the comparison of antihypertensive effects in patients with mild to moderate essential hypertension, at a dose of 60 mg to 120 mg of drugs between Fimasartan potassium and Losartan which is a representative compound of the ARB class, it was demonstrated that antihypertensive effects in terms of changes in diastolic blood pressure (DBP) in the sitting position at Week 12 of drug administration were respectively $-11.26 \pm 7.53$ mmHg for the Fimasartan-treated group and $-8.56 \pm 7.72$ mmHg for the Losartan-treated group, relative to a baseline, thus showing that antihypertensive effects after 12- or 24-week administration were higher in Fimasartan than Losartan (A Randomized, Double-blind, Losartan-controlled, Parallel Group Comparison Dose Titration Clinical Study to Evaluate the Antihypertensive Efficacy and Safety of Fimasartan (BR-A-657.K) 60 mg~120 mg in Patients with Mild to Moderate Essential Hypertension (Phase III)).

Amlodipine is a calcium channel blocker (CCB), and blocks an inflow of calcium ions to cell membranes of cardiac and peripheral vascular smooth muscles and therefore directly relaxes vascular smooth muscles to exhibit antihypertensive effects. Although the action mechanism by which Amlodipine mitigates angina pectoris has not been fully understood, it was found that the following two action mechanisms function to relieve ischemic symptoms.

First, Amlodipine dilates peripheral arteries to decrease the total peripheral resistance (after-load), thus leading to decreased cardiac work, and stabilizes a heart rate to decrease cardiac energy consumption and oxygen demand.

Second, it is believed that Amlodipine dilates main coronary arteries and other coronary arterioles of ischemic lesions and normal regions. Such vasodilation plays a role to increase delivery of oxygen to myocardial ischemic lesions of patients with coronary artery convulsion.

Although active research for the treatment of hypertension has recently been focused on a combination preparation of Amlodipine, which is a calcium channel blocker, with a compound belonging to the ARB class, such a combination preparation may present additional problems in some cases, such as by causing drug-to-drug interaction and increased adverse side effects of individual drugs.

To this end, the inventors of the present invention have recognized problems of simple combination preparations of Amlodipine and ARB class compounds and conducted a variety of extensive and intensive studies to address the foregoing problems. As a result, the present invention has been completed.

[Related technique]
1. KR 1989-0011854 A 1989 Aug. 22
2. WO 00/16773 1999 Sep. 8
3. KR 2001-0013626 A 2001 Feb. 26
4. KR 2001-0079517 A 2001 Aug. 22
5. KR 2001-0090193 A 2001 Oct. 18
6. KR 2004-0032639 2004 Apr. 17
7. KR 2010-0048137 2010 May 11
8. Yoo S D et al., Simultaneous determination of fimasartan, a novel antihypertensive agent, and its active metabolite in rat plasma by liquid chromatography-tandem mass spectrometry, Biomed Chromatogr. 2011 Jan. 26. doi:10.1002/bmc. 1592. Epub ahead of print
9. Yu K S, et al., Effect of multiple doses of fimasartan, an angiotensin II receptor antagonist, on the steady-state pharmacokinetics of digoxin in healthy volunteers. *Int J Clin Pharmacol Ther.* 2011 May; 49(5):321-327

10. Yu K S et al., The Effect of the Newly Developed Angiotensin Receptor II Antagonist Fimasartan on the Pharmacokinetics of Atorvastatin in relation to OATP1B1 in Healthy Male Volunteers. *J Cardiovasc Pharmacol.* 2011 Jul. 14. (Epub ahead of print)

DISCLOSURE OF THE INVENTION

Technical Problem

Therefore, the present invention is intended to provide an antihypertensive pharmaceutical composition which is effective not only for the prevention, alleviation and treatment of hypertension, but also for the prevention, alleviation or treatment of complications of hypertension and/or hyperlipidemia.

Technical Solution

The present invention provides an antihypertensive pharmaceutical composition containing Fimasartan, a pharmaceutically acceptable salt thereof, a solvate thereof or a hydrate thereof as an angiotensin II receptor blocker; and Amlodipine, an isomer thereof, a pharmaceutically acceptable salt thereof, a solvate thereof or a hydrate thereof as a calcium channel blocker.

In the present invention, Fimasartan, a pharmaceutically acceptable salt thereof, a solvate thereof or a hydrate thereof may be crystalline or amorphous. Crystalline and/or amorphous forms thereof also fall within the scope of the present invention.

In the present invention, Amlodipine, an isomer thereof, a pharmaceutically acceptable salt thereof, a solvate thereof or a hydrate thereof may be crystalline or amorphous. Crystalline and/or amorphous forms thereof also fall within the scope of the present invention.

As used herein, the term "pharmaceutically acceptable salt" refers to a salt with an inorganic acid, organic acid or metal, which has been conventionally used in the preparation of pharmaceutical products by pharmaceutical manufacturers. Examples of the inorganic acid include hydrochloric acid, hydrobromic acid, sulfuric acid, and phosphoric acid. Examples of the organic acid include citric acid, acetic acid, lactic acid, tartaric acid, fumaric acid, formic acid, propionic acid, oxalic acid, trifluoroacetic acid, methanesulfonic acid, benzenesulfonic acid (besylate), maleic acid, benzoic acid, gluconic acid, glycolic acid, succinic acid, 4-morpholineethanesulfonic acid, camphorsulfonic acid (camsylate), 4-nitrobenzenesulfonic acid, hydroxy-o-sulfonic acid, 4-toluenesulfonic acid, galacturonic acid, embonic acid, glutamic acid, aspartic acid and adipic acid (adipate). Examples of the metal include sodium, potassium, calcium and magnesium.

In the present invention, the angiotensin II receptor blocker is preferably a Fimasartan potassium salt, hydrochloride, calcium salt, sulfate, adipate, camsylate or besylate, and more preferably a Fimasartan potassium salt or Fimasartan potassium trihydrate. These materials are commercially available or otherwise may be prepared by using a known method (for example, see Korean Patent Nos. 0354654 and 0521980).

In the present invention, the calcium channel blocker is preferably an Amlodipine besylate, sulfate, camsylate, hydrochloride, potassium salt, calcium salt or adipate, and more preferably Amlodipine besylate. These materials are commercially available or otherwise may be prepared by using a known method (for example, see U.S. Pat. No. 4,572,909).

In the present invention, the solvent in the "solvate" refers to a common organic solvent which has been used in the preparation of organic compounds. Examples of the solvent include, but are not limited to, methanol, ethanol, 1-propanol, 2-propanol, 1-butanol, 2-butanol, 1-acetate, acetone, acetic acid, anisole, tetrahydrofuran, methyl acetate, ethyl acetate, propyl acetate, isopropyl acetate, isobutyl acetate, n-butyl acetate, dimethyl sulfoxide, pentane, and heptane.

In the present invention, the content of "hydrate" and "solvate" may be in a range of 0.25 to 10 moles relative to 1 mole of Fimasartan or Amlodipine, for example, 0.5 moles, 1 mole, 1.5 moles, 2 moles, 2.5 moles, 3 moles or 5 moles, but the present invention is not limited thereto.

The composition of the present invention may contain an angiotensin II receptor blocker in an amount of 0.5 to 240 mg, preferably 50 to 180 mg, and more preferably 60 to 120 mg.

Further, the composition of the present invention may contain a calcium channel blocker in an amount of 0.1 to 20 mg, preferably 5 to 15 mg, and more preferably 5 to 10 mg.

On the other hand, it is known that a conventional high dose (that is, pharmaceutically acceptable high dose/administration) of these drugs contained in a pharmaceutical composition is a maximum of 240 mg or less for Fimasartan and a maximum of 20 mg or less for Amlodipine, for an ordinary adult weighing 60 kg.

Throughout the specification, unless otherwise specifically indicated, the term "pharmaceutical composition" is intended to generally cover not only a single dosage form which is taken or administered at one single dose, such as tablet, capsule or injection, but also plural dosage forms which are administered at two or more divided doses. For example, the term "pharmaceutical composition containing Fimasartan, a pharmaceutically acceptable salt thereof, a solvate thereof or a hydrate thereof as an angiotensin II receptor blocker; and Amlodipine, an isomer thereof, a pharmaceutically acceptable salt thereof, a solvate thereof or a hydrate thereof as a calcium channel blocker" is interpreted to designate not only a single dosage form containing these two active ingredients all together, but also two dosage forms in which each contains one active ingredient. That is, where these two dosage forms are simultaneously administered or are consecutively administered at regular intervals and therefore effective amounts of two active ingredients contained in each of these dosage forms coexist in vivo to bring about synergistic effects, these two dosage forms also fall within the scope of the "pharmaceutical composition containing Fimasartan, a pharmaceutically acceptable salt thereof, a solvate thereof or a hydrate thereof as an angiotensin II receptor blocker; and Amlodipine, an isomer thereof, a pharmaceutically acceptable salt thereof, a solvate thereof or a hydrate thereof as a calcium channel blocker".

The composition of the present invention may further contain one or more pharmaceutically acceptable carriers besides the aforesaid ingredients, to be formulated into a variety of dosage forms for desired applications. Examples of the pharmaceutically acceptable carrier include saline, sterile water, Ringer's solution, buffered physiological saline, dextrose solution, maltodextrin solution, glycerol, and ethanol. These materials may be used alone or in any combination thereof. If necessary, other conventional additives may be added such as antioxidants, buffers and bacteriostatic agents.

Further, diluents, dispersants, surfactants, binders and lubricants may be additionally added to prepare injectable formulations such as aqueous solutions, suspensions, and emulsions, or oral formulations such as pills, capsules, granules, and tablets. Furthermore, the agent may be preferably formulated into a desired dosage form, depending on diseases to be treated and ingredients, using any appropriate method known in the art, or the method as disclosed in "Remington's Pharmaceutical Sciences, Mack Publishing Co., Easton, Pa.

The composition of the present invention may be administered via oral routes or parenteral routes (for example, intravenously, subcutaneously, intraperitoneally, or locally), depending on desired applications. The dose of the composition may vary depending on weight, age, gender, health status, and dietary habits of patients, administration times and routes, excretion rates, and severity of disease. The composition of the present invention may be administered once or several times a day.

The composition of the present invention may be an injectable formulation such as aqueous solution, suspension or emulsion, or an oral formulation such as pill, capsule, granule or tablet or in the form of a kit. An oral dosage form is preferable and a single tablet is more preferable.

Further, the composition of the present invention, due to having an enhanced antihypertensive effect, may be used for the prevention, alleviation or treatment of hypertension, heart failure, coronary heart disease, ischemic heart disease, ischemic peripheral vascular disease, hypertensive renal failure, cerebral apoplexy or arteriosclerosis.

Therefore, the present invention provides a pharmaceutical composition for the prevention, alleviation or treatment of hypertension, heart failure, coronary heart disease, ischemic heart disease, ischemic peripheral vascular disease, hypertensive renal failure, cerebral apoplexy or arteriosclerosis, containing Fimasartan, a pharmaceutically acceptable salt thereof, a solvate thereof or a hydrate thereof as an angiotensin II receptor blocker; and Amlodipine, an isomer thereof, a pharmaceutically acceptable salt thereof, a solvate thereof or a hydrate thereof as a calcium channel blocker.

Further, the present invention provides a method for the prevention, alleviation or treatment of hypertension, heart failure, coronary heart disease, ischemic heart disease, ischemic peripheral vascular disease, hypertensive renal failure, cerebral apoplexy or arteriosclerosis, including administering a composition containing an effective amount of Fimasartan, a pharmaceutically acceptable salt thereof, a solvate thereof or a hydrate thereof as an angiotensin II receptor blocker; and an effective amount of Amlodipine, an isomer thereof, a pharmaceutically acceptable salt thereof, a solvate thereof or a hydrate thereof as a calcium channel blocker to a mammal, including a human, in need thereof.

The present invention provides a method for preventing or treating a hypertension, comprising administering the antihypertensive pharmaceutical composition of the present invention to a mammal including a human.

In the method for preventing or treating a hypertension of the present invention, the antihypertensive pharmaceutical composition is comprised Fimasartan, a pharmaceutically acceptable salt thereof, a solvate thereof or a hydrate thereof as an angiotensin II receptor blocker; and Amlodipine, an isomer thereof, a pharmaceutically acceptable salt thereof, a solvate thereof or a hydrate thereof as a calcium channel blocker.

In the method for preventing or treating a hypertension of the present invention, the sort or content of each of the angiotensin II receptor blocker and the calcium channel blocker is the same as described above regarding the antihypertensive pharmaceutical composition of present invention.

In the method for preventing or treating a hypertension of the present invention, the angiotensin II receptor blocker is preferably a Fimasartan potassium salt, hydrochloride, calcium salt, sulfate, adipate, camsylate or besylate and more preferably is a Fimasartan potassium salt.

In the method for preventing or treating a hypertension of the present invention, the calcium channel blocker is preferably an Amlodipine besylate.

In the method for preventing or treating a hypertension of the present invention, the content of the angiotensin II receptor blocker is preferably in the range of 0.5 to 240 mg, and the content of the calcium channel blocker is in the range of 0.1 to 20 mg.

Further, the present invention provides a use of a composition containing an effective amount of Fimasartan, a pharmaceutically acceptable salt thereof, a solvate thereof or a hydrate thereof as an angiotensin II receptor blocker; and an effective amount of Amlodipine, an isomer thereof, a pharmaceutically acceptable salt thereof, a solvate thereof or a hydrate thereof as a calcium channel blocker, for manufacturing a pharmaceutical preparation for the prevention, alleviation or treatment of hypertension, heart failure, coronary heart disease, ischemic heart disease, ischemic peripheral vascular disease, hypertensive renal failure, cerebral apoplexy or arteriosclerosis.

Advantageous Effects

The composition of the present invention exhibits an enhanced antihypertensive effect greater than the simple sum of antihypertensive values of the same doses of individual active ingredients. Accordingly, the composition of the present invention enables the use of individual active ingredients at a content or dose lower than that upon separate use thereof, and thus can provide more effective treatment or prevention of hypertension or the like while reducing adverse side effects due to an overdose of individual active ingredients.

MODE FOR INVENTION

Now, the present invention will be described in more detail with reference to the following Examples. These examples are provided only for illustrating the present invention and should not be construed as limiting the scope and spirit of the present invention.

EXPERIMENTAL EXAMPLE

Antihypertensive Effects of Inventive Composition

This study is intended to examine antihypertensive action of individual drugs. For this purpose, test drugs, i.e., Fimasartan potassium trihydrate, Losartan potassium salt, Valsartan, Amlodipine besylate, a combination of Fimasartan potassium trihydrate with Amlodipine besylate, a combination of Losartan potassium salt with Amlodipine besylate, and a combination of Valsartan with Amlodipine besylate were repeatedly and orally administered for 4 weeks to rats with essential hypertension. Changes in blood pressure, heart rate and body weight of animals were measured to investigate the antihypertensive action by long-term administration of individual drugs, confirm the maintenance degree of effective and stable blood pressure, and examine the difference between single administration and combined administration of drugs. In this manner, the antihypertensive action was compared and evaluated between the individual drugs.

(1) Test Material and Method
1 Experimental Animals
8-week old male spontaneously hypertensive rats (SHR), weighing 230 to 250 g, were purchased from Charles River Japan (CRJ). The animals were used in the test, after being subjected to an acclimation period until the animals were 18 to 19-week old (340 to 380 g) to reach a mean blood pressure of 160 to 170 mmHg. Animals with a good condition were selected by minute observation over the acclimation period prior to the test, and divided into individual test groups, each consisting of 8 animals (n=8). Only the selected animals, from which a rise in blood pressure was confirmed using a non-invasive blood pressure monitoring system (CODA-6), were assigned to the test group. Through the measurement of SHR blood pressure prior to application of the main test, SHR individuals having blood pressure outside a blood pressure range (individuals exhibiting a mean blood pressure below 140 mmHg or above 220 mmHg as measured) of normal SHR were excluded from the test.

② Establishment of Drug-Treated Groups and Administration Method

A suitable dose capable of exhibiting a significant antihypertensive effect through a basic test and a preliminary test was taken as a final dose of drugs administered to experimental rats in this test. Low, medium and high doses of the drugs according to individual drugs were established in the preliminary test. Then, based on the test results, a dose capable of achieving significant lowering of a blood pressure from the blood pressure of hypertensive rats prior to administration of the drugs to a range of 20 to 50 mmHg after administration of the drugs (a dose corresponding to 20 to 25% of a usual clinical dose) was taken as an optimal dose of the single administration group. On the other hand, based on the review results from the literature, a dose capable of showing a stable antihypertensive action without causing toxicity at 4-week administration was set for the combination preparation-administered group. All the doses referred to those used in the already performed test. Doses and drug-administered groups used in the final main test are as follows.

As an ARB compound, Losartan potassium salt, Valsartan and Fimasartan potassium trihydrate were respectively purchased and used from Zhejiang Huahai Pharmaceutical Co., Ltd. 10 mg/kg of Losartan potassium salt was taken as an L group, and 10 mg/kg of Valsartan was taken as a V group. With regard to Fimasartan potassium trihydrate, 3 mg/kg was taken as an F1 group, and 10 mg/kg was taken as an F2 group.

As a calcium channel blocker, Amlodipine besylate (homemade by the method described in U.S. Pat. No. 4,572,909) was used. 0.5 mg/kg of Amlodipine besylate was taken as an A1 group, and a dose of 1.6 mg/kg was taken as an A2 group. The test materials and the comparative drugs were each suspended in 0.5% carboxymethylcellulose sodium salt (CMC—Na, Sigma) prior to using. As a control group, 0.5% CMC alone was administered.

③ Test Method

Administration: Upon carrying out the administration, the drug preparation was heated to a suitable temperature of 35° in a water bath, followed by forced oral administration of 5 mL/kg via a stomach sonde.

Measurement of blood pressure: Blood pressure of rats was measured as follows. Rats were restrained and placed in a heating device which was then heated to a temperature of about 40° (based on the temperature of 37° in a restraining cage) over 13 minutes, such that the tail blood vessels were engorged, and the blood pressure of rats was measured using CODA-6 equipment that monitors a blood pressure by means of the software of the main body through a pair of cuffs attached to the tail. The non-invasive blood pressure measuring method via CODA-6 (Kent Scientific Corporation) enables a long-term blood pressure measuring test that should involve repeated administration of test materials, which is not feasible with a direct blood pressure measuring method through arterial cannulation, such as conventionally used physiograph or power lab. In order to confirm a disappearance pattern in response to doses of drugs by 4-week repeated administration and a degree of recovery to initial blood pressure, the blood pressure was measured once a day for 1 week after the final administration was completed.

Changes in blood pressure were confirmed with focusing on changes in mean arterial pressure (MAP), and changes in diastolic and systolic blood pressure, heart rate, and body weight were used as references for other changes in the experimental results.

(2) Results Processing and Statistical Analysis

Statistical analysis of the measurement values obtained in this experiment was carried out using a statistical program SPSS. For items where a significant F value is observed in one-way ANOVA, the comparison was made at significant levels of $p<0.001$, 0.01 and 0.05 between the control group and the experimental groups with a different dose of drugs.

In the 4-week repeated administration efficacy test, all of the groups including the control group exhibited a slight increase in body weight. The body weight tended to decrease at the early stage of the test, but the maintenance of the body weight was confirmed after the middle stage of the test. This was believed to be a symptom resulting from exposure to stress during the indirect blood pressure measurement, such as heating and restraint, not direct effects due to drugs.

Based on the measured results, kinds and doses of the drugs administered to the individual drug-administered groups, in conjunction with antihypertensive values obtained in the individual drug-administered groups, that is, the antihypertensive degree over 4 weeks in response to the drug administration, as calculated based on the blood pressure prior to administration of drugs, are given in Table 1 below.

TABLE 1

Antihypertensive degree (mmHg) with consecutive 4-week administration of drugs, as compared to blood pressure prior to administration

| Drug-administered groups (kinds and doses of drugs) | Mean | Standard error |
|---|---|---|
| Example 1 (F1 + A1) | −55 | 2.255 |
| Example 2 (F2 + A2) | −75 | 2.536 |
| Comparative Example 1 (F1) | −35 | 1.375 |
| Comparative Example 2 (F2) | −50 | 2.135 |
| Comparative Example 3 (L) | −20 | 1.256 |
| Comparative Example 4 (V) | −32 | 2.862 |
| Comparative Example 5 (A1) | −13 | 1.105 |
| Comparative Example 6 (A2) | −20 | 1.325 |
| Comparative Example 7 (L + A2) | −32 | 2.268 |
| Comparative Example 8 (V + A2) | −46 | 2.675 |

As shown in Table 1 above, it can be seen that Comparative Example 1 exhibited a superior antihypertensive effect even with administration of a dose lower than a usual clinical dose (usual clinical dose of Fimasartan potassium trihydrate=60 mg, usual clinical dose of Losartan potassium salt=50 mg, and usual clinical dose of Valsartan=80 mg), as compared to Comparative Example 3 and Comparative Example 4.

Further, Examples 1 and 2, which use a combination preparation of Fimasartan and Amlodipine that is the composition of the present invention, exhibited an antihypertensive effect greater than a simple sum of antihypertensive effects obtained when each ingredient alone was administered. For example, as compared to an antihypertensive value of −13 mmHg for single administration of 0.5 mg/Kg of Amlodipine besylate (Comparative Example 5) and an antihypertensive value of −35 mmHg for single administration of 3 mg/Kg of Fimasartan potassium trihydrate (Comparative Example 1), Example 1 corresponding to a combination preparation of both drugs (Amlodipine besylate and Fimasartan potassium trihydrate) exhibited an antihypertensive value of −55 mmHg which corresponds to an enhanced antihypertensive effect greater than a simple sum of antihypertensive values of two drugs. This effect is a significant numerical value even upon taking into consideration a standard error. Further, as compared to an antihypertensive value of −20 mmHg for single administration of 1.6 mg/Kg of Amlodipine besylate (Comparative Example 6) and an antihypertensive value of −50 mmHg for single administration of 10 mg/Kg of Fimasartan potassium trihydrate (Comparative Example 2), Example 2 corresponding to a combination preparation of both drugs exhibited an antihypertensive value of −75 mmHg which corresponds to an enhanced antihypertensive effect greater than a simple sum of antihypertensive values of two drugs. This effect is confirmed to be an unexpected remarkable effect, when compared with the foregoing results (Comparative Examples 7 and 8) wherein a combination preparation of another ARB compound and Amlodipine exhibited an antihypertensive value smaller than a simple sum of antihypertensive values of individual ingredients of the combination preparation.

As described above, since the composition of the present invention exhibits an antihypertensive effect greater than the sum of antihypertensive effects obtained when each active ingredient alone was administered (synergistic effect), the risk of adverse side effects due to an overdose of individual active ingredients can also be greatly reduced by further decreasing the content of each active ingredient, and inconveniences associated with medication of patients upon performing combination therapy of individual active ingredients can be solved.

PREPARATION EXAMPLE

Preparation of Composition (Tablet) of the Present Invention

The composition of the present invention was formulated into tablets containing ingredients and contents thereof as described in Table 2 below, each of which is expressed as Preparation Examples 1 to 4.

TABLE 2

| Ingredients | Preparation Example 1 (mg/tablet) | Preparation Example 2 (mg/tablet) | Preparation Example 3 (mg/tablet) | Preparation Example 4 (mg/tablet) |
|---|---|---|---|---|
| Fimasartan potassium trihydrate | 66.01 | 132.02 | 66.01 | 132.02 |
| Amlodipine besylate | 6.99 | 6.99 | 13.98 | 13.98 |
| Corn starch | 46 | 98.99 | 39.01 | 92 |
| Microcrystalline cellulose | 16 | 32 | 16 | 32 |
| Crospovidone | 10 | 20 | 10 | 20 |
| Hydroxypropylcellulose | 3.5 | 7 | 3.5 | 7 |
| Magnesium stearate | 1.5 | 3 | 1.5 | 3 |
| Total weight/tablet (mg) | 150 | 300 | 150 | 300 |

Preparation of Tablets

Fimasartan potassium trihydrate, Amlodipine besylate, corn starch, microcrystalline cellulose and crospovidone were placed in a high-speed mixer, followed by mixing. In addition, hydroxypropylcellulose and purified water (q.s.) were mixed to prepare a binding solution which was then added to the high-speed mixer where the pre-mixed powder was placed, followed by granulation. The resulting granules were dried in a drier. The dried granules were sieved through a No. 20 sieve and magnesium stearate was added thereto, followed by mixing to obtain a final mixture. The final mixture was compressed into tablets corresponding to Preparation Examples 1 to 4, using a rotary tablet press.

Since modifications will be apparent to those of skill in this art, it is intended that this invention be limited only by the scope of the appended claims.

What is claimed is:

1. An antihypertensive pharmaceutical composition, comprising:
   Fimasartan, a pharmaceutically acceptable salt thereof, a solvate thereof or a hydrate thereof as an angiotensin II receptor blocker; and
   Amlodipine, an isomer thereof, a pharmaceutically acceptable salt thereof, a solvate thereof or a hydrate thereof as a calcium channel blocker.

2. The antihypertensive pharmaceutical composition of claim 1, wherein the angiotensin II receptor blocker is a Fimasartan potassium salt, hydrochloride, calcium salt, sulfate, adipate, camsylate or besylate.

3. The antihypertensive pharmaceutical composition of claim 2, wherein the angiotensin II receptor blocker is a Fimasartan potassium salt.

4. The antihypertensive pharmaceutical composition of claim 1, wherein the angiotensin II receptor blocker is a Fimasartan potassium trihydrate.

5. The antihypertensive pharmaceutical composition of claim 1, wherein the calcium channel blocker is an Amlodipine besylate, sulfate, camsylate, hydrochloride, potassium salt, calcium salt or adipate.

6. The antihypertensive pharmaceutical composition of claim 5, wherein the calcium channel blocker is an Amlodipine besylate.

7. The antihypertensive pharmaceutical composition of claim 1, wherein the amount of the angiotensin II receptor blocker is in the range of 0.5 to 240 mg, and the amount of the calcium channel blocker is in the range of 0.1 to 20 mg.

8. The antihypertensive pharmaceutical composition of claim 7, wherein the amount of the angiotensin II receptor blocker is in the range of 50 to 180 mg.

9. The antihypertensive pharmaceutical composition of claim 8, wherein the amount of the angiotensin II receptor blocker is in the range of 60 to 120 mg.

10. The antihypertensive pharmaceutical composition of claim 7, wherein the amount of the calcium channel blocker is in the range of 5 to 15 mg.

11. The antihypertensive pharmaceutical composition of claim 10, wherein the amount of the calcium channel blocker is in the range of 5 to 10 mg.

12. The antihypertensive pharmaceutical composition of claim 1, wherein the pharmaceutical composition is an oral dosage form.

13. The antihypertensive pharmaceutical composition of claim 12, wherein the dosage form is a single tablet.

14. A method for the alleviation or treatment of hypertension, heart failure, coronary heart disease, ischemic heart disease, ischemic peripheral vascular disease, hypertensive renal failure, cerebral apoplexy or arteriosclerosis, comprising administering simultaneously or consecutively to a mammal in need thereof:
   Fimasartan, a pharmaceutically acceptable salt thereof, a solvate thereof or a hydrate thereof as an angiotensin II receptor blocker; and
   Amlodipine, an isomer thereof, a pharmaceutically acceptable salt thereof, a solvate thereof or a hydrate thereof as a calcium channel blocker.

15. A method for treating a hypertension, comprising administering to a mammal an antihypertensive pharmaceutical composition comprising:
   Fimasartan, a pharmaceutically acceptable salt thereof, a solvate thereof or a hydrate thereof as an angiotensin II receptor blocker; and
   Amlodipine, an isomer thereof, a pharmaceutically acceptable salt thereof, a solvate thereof or a hydrate thereof as a calcium channel blocker.

16. The method of claim 15, wherein the mammal is a human.

17. The method of claim 15, wherein the angiotensin II receptor blocker is a Fimasartan potassium salt, hydrochloride, calcium salt, sulfate, adipate, camsylate or besylate.

18. The method of claim 17, wherein the angiotensin II receptor blocker is a Fimasartan potassium salt.

19. The method of claim 15, wherein the calcium channel blocker is an Amlodipine besylate.

20. The method of claim 15, wherein the amount of the angiotensin II receptor blocker is in the range of 0.5 to 240 mg, and the amount of the calcium channel blocker is in the range of 0.1 to 20 mg.

* * * * *

UNITED STATES PATENT AND TRADEMARK OFFICE
CERTIFICATE OF CORRECTION

PATENT NO. : 8,765,776 B2  
APPLICATION NO. : 13/205545  
DATED : July 1, 2014  
INVENTOR(S) : Seung Ho Kim et al.

Page 1 of 1

It is certified that error appears in the above-identified patent and that said Letters Patent is hereby corrected as shown below:

IN THE TITLE PAGES:

In Item (75) Inventors:

Page 1, lines 4-5, "Je Hak Kim, Anyang-si (KR)" should read —Je Hak Kim, Gyeonggi-do (KR)—.

Page 1, lines 5-6, "Kyung Wan Nam, Gunpo-si (KR)" should read —Kyung Wan Nam, Gyeonggi-do (KR)—.

Page 1, lines 6-7, "Yong Ha Chi, Yongin-si (KR)" should read —Yong Ha Chi, Gyeonggi-do (KR)—.

Page 1, lines 7-8, "Soo Heui Paik, Ansan-si (KR)" should read —Soo Heui Paik, Gyeonggi-do (KR)—.

Signed and Sealed this  
Fourth Day of November, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,765,776 B2  
APPLICATION NO. : 13/205545  
DATED : July 1, 2014  
INVENTOR(S) : Kim et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this  
Twelfth Day of January, 2016

Michelle K. Lee  
*Director of the United States Patent and Trademark Office*